(12) United States Patent
Iaccino et al.

(10) Patent No.: US 7,728,186 B2
(45) Date of Patent: Jun. 1, 2010

(54) PRODUCTION OF AROMATICS FROM METHANE

(75) Inventors: Larry L. Iaccino, Seabrook, TX (US); Neeraj Sangar, League City, TX (US); Elizabeth L. Stavens, Seabrook, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 698 days.

(21) Appl. No.: 11/732,860

(22) Filed: Apr. 5, 2007

(65) Prior Publication Data

US 2007/0249740 A1    Oct. 25, 2007

Related U.S. Application Data

(60) Provisional application No. 60/794,281, filed on Apr. 21, 2006.

(51) Int. Cl.
*C07C 15/00* (2006.01)
*C07C 2/52* (2006.01)

(52) U.S. Cl. .............. 585/407; 585/418; 585/419; 585/420; 585/943

(58) Field of Classification Search ............ 585/407, 585/418, 419, 420, 943
See application file for complete search history.

(56) References Cited

U.S. PATENT DOCUMENTS

| | | | |
|---|---|---|---|
| 4,727,206 A | 2/1988 | Clayson et al. | |
| 5,026,937 A | 6/1991 | Bricker | |
| 5,336,825 A | 8/1994 | Choudhary et al. | |
| 6,239,057 B1 | 5/2001 | Ichikawa et al. | |
| 6,426,442 B1 | 7/2002 | Ichikawa et al. | |
| 2002/0072642 A1 | 6/2002 | Allison et al. | |
| 2003/0083535 A1 | 5/2003 | Wright et al. | |

FOREIGN PATENT DOCUMENTS

| | | |
|---|---|---|
| JP | 9-238280 | 9/1997 |
| JP | 2002-84467 | 3/2002 |
| WO | 03/000826 | 1/2003 |
| WO | 2006/083409 | 8/2006 |

OTHER PUBLICATIONS

Japanese Office Action issued in Japanese Patent Application No. JP 2003-049234, dated Nov. 21, 2007, and translation.
Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

*Primary Examiner*—Jafar Parsa
(74) *Attorney, Agent, or Firm*—Andrew B. Griffis

(57) ABSTRACT

In a process for converting methane to aromatic hydrocarbons, a feed containing methane is contacted with a dehydrocyclization catalyst in a reaction zone under conditions including a first maximum temperature effective to convert the methane to aromatic hydrocarbons and generate coke on the catalyst. A portion of the coked catalyst is transferred from the reaction zone to a separate regeneration zone, where the catalyst portion is contacted with a regeneration gas under conditions including a second maximum temperature less than or equal to the first maximum temperature and effective to at least partially remove coke from the catalyst portion. Before being returned to the reaction zone, the regenerated catalyst portion is contacted with a carburizing gas in a catalyst treatment zone separate from the reaction zone at a third maximum temperature less than the first maximum temperature.

52 Claims, 1 Drawing Sheet

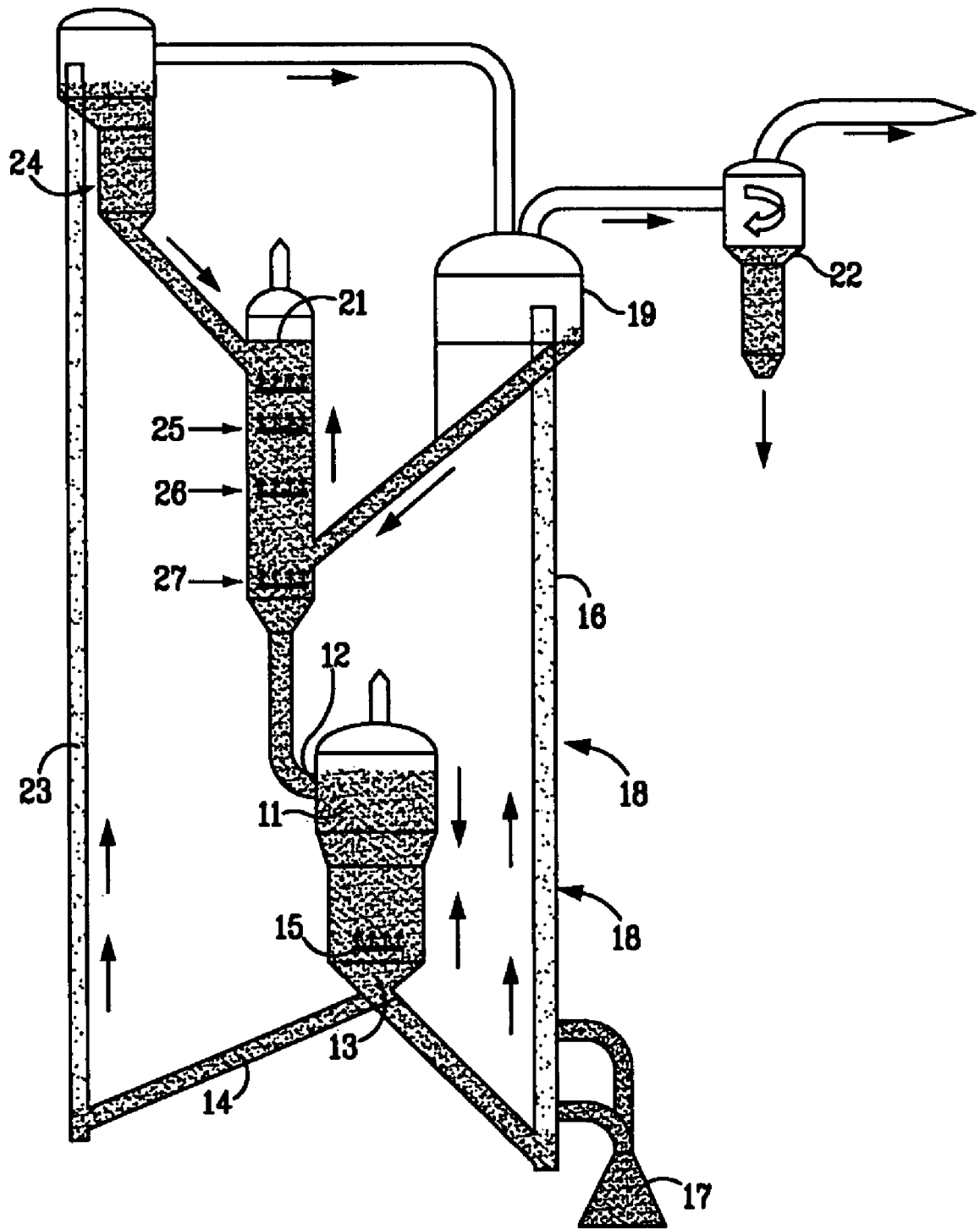

PRODUCTION OF AROMATICS FROM METHANE

CROSS REFERENCE TO RELATED APPLICATIONS

This application claims the benefit of Provisional Application No. 60/794,281 filed Apr. 21, 2006, the disclosures of which are incorporated by reference in their entireties.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

However, the successful application of reductive coupling to produce aromatics on a commercial scale requires the solution of a number of serious technical challenges. For example, the reductive coupling process is both endothermic and thermodynamically limited. Thus the cooling effect caused by the reaction lowers the reaction temperature sufficiently to greatly reduce the reaction rate and total thermodynamic conversion if significant make-up heat is not provided to the process.

Moreover, the process tends to produce carbon and other non-volatile materials that accumulate on the catalyst resulting in reduced activity and potentially undesirable selectivity shifts. In addition, at the high temperatures involved in the process, the active metal species ($MoC_x$, $WC_x$, etc) on the catalyst may migrate, agglomerate or change phase, again resulting in undesirable declines in conversion and selectivity. The catalyst is therefore subjected to frequent oxidative regeneration to remove the carbon and other non-volatile materials that have accumulated on the catalyst and possibly to redistribute the active metal species. However, depending on the composition of the catalyst, oxidative regeneration may have certain unwanted ancillary effects. For example, the metal on the catalyst may be converted from a catalytically active elemental or carburized state to a less active oxidized state. Also, following regeneration, the catalyst may exhibit enhanced activity for coke deposition and related hydrogen generation. Thus the present invention seeks to provide an improved method for regenerating a dehydroaromatization catalyst and subsequently tailoring its activity for use in the conversion of methane to aromatic hydrocarbons.

U.S. Patent Application Publication No 2003/0083535 discloses a process for aromatization of a methane-containing feed, in which a dehydroaromatization catalyst is circulated between a reactor system and a regenerator system, where the catalyst is contacted with different regeneration gases, including $O_2$, $H_2$, and $H_2O$, at different times to regenerate different portions of catalyst. The percentage of catalyst contacting each regeneration gas is controlled to maintain the reactor system and regeneration system under a heat balance regime. The reactor system includes a fluidized bed of catalyst in a riser reactor, and the regeneration system includes a second fluidized bed of catalyst maintained in a bubbling bed reactor. After passage through the regeneration system, the hot regenerated catalyst is returned to the reactor system by way of a transfer system, which may include a reduction vessel for increasing the activity of the regenerated catalyst by contacting the catalyst in a fluidized bed with a reducing gas stream including hydrogen and/or methane.

However, processes that use the catalyst regeneration step to supply reaction heat, such as that described in the '535 publication, suffer from the problem that the catalyst needs to be heated well above the target reaction temperature in the regeneration process, which leads to accelerated catalyst degradation and hence reduced catalyst life. In addition, the entire catalyst inventory must be circulated between the reactor system and the regenerator system and hence is subject to the extreme conditions in the regenerator. Moreover, to maintain heat balance, the process requires a high selectivity to coke rather than to the desired aromatic products.

SUMMARY

In one aspect, the present invention resides in a process for converting methane to higher hydrocarbons including aromatic hydrocarbons, the process comprising:

(a) contacting a feed containing methane with a dehydrocyclization catalyst in a reaction zone under conditions comprising a first maximum temperature effective to convert said methane to aromatic hydrocarbons and generate coke on the catalyst;

(b) transferring a portion of said catalyst from the reaction zone to a regeneration zone separate from said reaction zone;

(c) contacting said catalyst portion with a regeneration gas in said regeneration zone under conditions effective to at least partially remove coke from said catalyst portion and comprising a second maximum temperature less than or equal to said first maximum temperature;

(d) contacting the regenerated catalyst portion with a carburizing gas in a catalyst treatment zone separate from said reaction zone under conditions comprising a third maximum temperature less than or equal to said first maximum temperature; and (e) returning the catalyst portion to the reaction zone.

In one embodiment, said third maximum temperature is greater than said second maximum temperature. Conveniently, said first maximum temperature is from about 700° C. to about 1200° C., such as from about 800° C. to about 950° C.; said second maximum temperature is from about 400° C. to about 900° C., such as from about 500° C. to about 700° C. and said third maximum temperature is from about 400° C. to about 1100° C., such as from about 500° C. to about 900° C.

Conveniently, heat is supplied to said catalyst portion and/or said carburizing gas prior to or during said contacting (d).

In one embodiment, said catalyst portion and said carburizing gas flow in opposite directions in said catalyst treatment zone. Conveniently, said catalyst treatment zone comprises a settling bed reactor or at least one fluidized bed reactor.

Generally, the dehydrocyclization catalyst comprises a metal at least partly present in elemental form or as a carbide species during the contacting (a), wherein the contacting (c) at least partly converts said metal to an oxide form, and the contacting (d) at least partly returns the metal to the elemental or carbide form.

In another aspect, the invention resides in a process for converting methane to higher hydrocarbons including aromatic hydrocarbons, the process comprising;

(a) contacting a dehydrocyclization catalyst with a carburizing gas under carburizing conditions in a catalyst treatment zone;

(b) transferring said dehydrocyclization catalyst portion from (a) to a reaction zone separate from the catalyst treatment zone; and (c) contacting a feed containing methane with said dehydrocyclization catalyst in the reaction zone under dehydrocyclization conditions effective to convert said methane to aromatic hydrocarbons, wherein said dehydrocyclization conditions comprise a first maximum temperature and said carburizing conditions comprise a further maximum temperature less than or equal to the first maximum temperature.

In a further aspect, the invention resides in a process for converting methane to higher hydrocarbons including aromatic hydrocarbons, the process comprising:

(a) contacting a feed containing methane with a dehydrocyclization catalyst in a reaction zone under conditions effective to convert said methane to aromatic hydrocarbons and generate coke on the catalyst, said conditions comprising a first maximum temperature and said dehydrocyclization catalyst including a metal at least partly present in elemental form or as a carbide species;

(b) transferring a first portion of said catalyst from the reaction zone to a heating zone separate from said reaction zone;

(c) heating the first catalyst portion in the heating zone by direct contact of the catalyst with hot combustion gases generated by burning a supplemental source of fuel;

(d) transferring a second portion of said catalyst from said reaction zone to a regeneration zone separate from said reaction zone and said heating zone;

(e) contacting said second catalyst portion with a regeneration gas in said regeneration zone under conditions comprising a second maximum temperature less than or equal to said first maximum temperature and effective to at least partially remove coke from said second catalyst portion and to at least partly convert the metal of said second catalyst portion to an oxide species;

(f) transferring the regenerated second catalyst portion from the regeneration zone to a catalyst treatment zone separate from the reaction zone, the heating zone and the regeneration zone;

(g) contacting the regenerated second catalyst portion with a carburizing gas in said catalyst treatment zone under conditions effective to at least partly return the metal of said second catalyst portion to an elemental form or to a carbide species; and (h) returning the first and second catalyst portions to the reaction zone.

Conveniently, the heated first catalyst portion is also transferred to the catalyst treatment zone for contacting with a carburizing gas.

In one embodiment, said carburizing gas comprises hydrogen and at least one of CO and $CO_2$.

In another embodiment, the carburizing gas comprises at least one hydrocarbon and typically comprises at least one of methane, ethane, propane, butane, isobutene, benzene and naphthalene. Conveniently, said hydrocarbon-containing gas also comprises at least one of $CO_2$, CO, $H_2$, $H_2O$ and inert diluents.

In one embodiment, the metal comprises at least one of molybdenum, tungsten, zinc and rhenium and the dehydrocyclization catalyst also comprises an inorganic support, such as alumina, silica or ZSM-5.

In yet a further aspect, the invention resides in a process for converting methane to higher hydrocarbons including aromatic hydrocarbons, the process comprising:

(a) contacting a feed containing methane with a dehydrocyclization catalyst in a reaction zone with an inverse temperature profile under conditions effective to convert said methane to aromatic hydrocarbons and generate coke on the catalyst, and said dehydrocyclization catalyst including a metal at least partly present in elemental form or as a carbide species;

(b) transferring a portion of said catalyst from the reaction zone to a heating zone separate from said reaction zone;

(c) heating the catalyst portion in the heating zone by direct contact of the catalyst with hot combustion gases generated by burning a supplemental source of fuel;

(d) contacting said heated catalyst portion with a regeneration gas in said regeneration zone under conditions effective to at least partially remove coke from said catalyst portion;

(e) transferring the regenerated catalyst portion from the regeneration zone to a catalyst treatment zone separate from the reaction zone, the heating zone and the regeneration zone;

(f) contacting the regenerated catalyst portion with a carburizing gas in said catalyst treatment zone under conditions effective to at least partly return the metal of said catalyst portion to an elemental form or to a carbide species; and (g) returning the catalyst portion to the reaction zone.

Conveniently, fresh dehydrocyclization catalyst is introduced to the process at (f).

In still yet a further aspect, the invention resides in a process for converting methane to higher hydrocarbons including aromatic hydrocarbons, the process comprising:

(a) introducing a fresh metal-containing dehydrocyclization catalyst portion to a catalyst treatment zone;

(b) contacting the fresh dehydrocyclization catalyst with a carburizing gas in said catalyst treatment zone under conditions effective to at least partly convert the metal of said catalyst to an elemental form or to a carbide species and/or reduce coke-selective sites;

(c) transferring said treated dehydrocyclization catalyst from the catalyst treatment zone to a reaction zone separate from the catalyst treatment zone;

(d) contacting a feed containing methane with said treated dehydrocyclization catalyst in said reaction zone under conditions effective to convert said methane to aromatic hydrocarbons and generate an inverse temperature profile in the reaction zone;

(e) transferring a portion of said catalyst from the reaction zone to a heating zone separate from said reaction zone and the catalyst treatment zone;

(f) heating the catalyst portion in the heating zone by direct contact of the catalyst portion with hot combustion gases generated by burning a supplemental source of fuel; and (g) returning the catalyst portion to the reaction zone.

BRIEF DESCRIPTION OF THE DRAWINGS

FIG. 1 is a diagram of a process for converting methane to higher hydrocarbons according to a first embodiment of the invention.

DETAILED DESCRIPTION OF THE EMBODIMENTS

As used herein the term "higher hydrocarbon(s)" means hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) comprising at least one carbon atom and at least one non-hydrogen atom, e.g., methanol, ethanol, methylamine, and/or ethylamine.

As used herein the term "aromatic hydrocarbon(s)" means molecules containing one or more aromatic rings. Examples of aromatic hydrocarbons are benzene, toluene, xylenes, naphthalene, and methylnaphthalenes.

As used herein the term "moving bed" reactor means a zone or vessel with contacting of solids and gas flows such that the superficial gas velocity (U) is below the velocity required for dilute-phase pneumatic conveying of solid particles in order to maintain a solids bed with void fraction below 95%. A moving-bed reactor may operate under several flow regimes including settling- or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$). These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Butterworth-Heinemann, Boston, 1990.

As used herein the term "settling bed" means a zone or vessel wherein particulates contact with gas flows such that the superficial gas velocity (U) is below the minimum velocity required to fluidize the solid particles, the minimum fluidization velocity ($U_{mf}$), $U<U_{mf}$, in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example Chapter 3 of "Fluidization Engineering," D. Kunii and O. Levenspiel, $2^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "fluidized bed" reactor means a zone or vessel with contacting of solids and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein the term "cascaded fluid-beds" means a series arrangement of individual fluid-beds such that there can be a gradient in gas and/or solid property (such as, temperature, gas or solid composition, pressure etc.) as the solid or gas cascades from one fluid-bed to another. Locus of minimum fluidization velocity is given in, for example, the Kunii and Walas publications noted above.

As used herein the term "riser" reactor means a zone or vessel (such as, vertical cylindrical pipe) used for net upwards transport of solids in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in the Kunii and Walas publications noted above.

As used herein the term "carburizing gas" means any gas that, under the conditions in the catalyst treatment zone, can at least partially convert the metal of said second catalyst portion from the oxidized form produced in the regeneration zone to an elemental form or to a carbide species or can also at least partially coke highly active sites that may have been produced on the support of said second catalyst portion during regeneration. The carburizing gas will normally comprise at least one hydrocarbon, but can also comprise a mixture of hydrogen and at least one of CO and $CO_2$.

The present invention provides a process for producing aromatic hydrocarbons by contacting a feedstock containing methane, typically together with $H_2$, CO and/or $CO_2$, with a dehydrocyclization catalyst in a reaction zone under conditions effective to convert the methane to aromatic hydrocarbons and hydrogen. As the reaction proceeds, coke builds up on the catalyst thereby reducing the activity of the catalyst and hence a portion of the catalyst is continuously or intermittently withdrawn from the reaction zone and passed through a separate regeneration zone, where the coked catalyst is contacted with an oxygen-containing regeneration atmosphere. The regeneration reaction is exothermic and to avoid damage to the catalyst, the conditions in the regeneration zone are controlled so that the maximum temperature reached in the regeneration zone is less than or equal to the maximum temperature in the dehydrocyclization reaction zone.

Under the oxidizing conditions in the regeneration zone, coke is burnt from the catalyst but at the same time the activity of the catalyst tends to be adversely affected, either by conversion of elemental metal or metal carbides on the catalyst to oxide forms and/or by generation of coke selective sites, such as highly acid sites, on the catalyst. According to the invention, the regenerated catalyst is transferred to a catalyst treatment zone separate from the reaction zone and the regeneration zone, where the regenerated catalyst is contacted with a carburizing gas under conditions which favor conversion of metal oxides on the regenerated catalyst back to carbide species or the elemental form as well as enhancing the aromatics selectivity of the catalyst. The use of the separate catalyst treatment zone allows any by-products, such as hydrogen, generated as a result of the contact with the carburizing gas to be removed from the catalyst treatment zone without being combined with the effluent from the reaction zone.

As discussed above, the dehydrocyclization reaction is endothermic and the present invention also provides a method for supplying heat to the reaction by withdrawing a further portion of the catalyst from the reaction zone, heating the further catalyst portion in a heating zone with hot combustion gases generated by burning a supplemental source of fuel and then returning the heated catalyst portion to the reaction zone. The heated catalyst portion is conveniently fed to the catalyst treatment zone for contact with the carburizing gas before being returned to the reaction zone.

In addition, the invention provides a process for utilizing the hydrogen generated as a by-product of the dehydrocyclization reaction and in particular to a process for converting at least part of the hydrogen to higher value products.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in the hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$ hydrocarbons.

Dehydrocyclization

In the dehydrocyclization step of the present process, the methane containing feedstock is contacted with a dehydrocyclization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4 + 2H_2 \quad \text{(Reaction 1)}$$

$$6CH_4 \leftrightarrow C_6H_6 + 9H_2 \quad \text{(Reaction 2)}$$

$$10CH_4 \leftrightarrow C_{10}H_8 + 16H_2 \quad \text{(Reaction 3)}$$

Carbon monoxide and/or dioxide that may be present in the feed improves catalyst activity and stability by facilitating reactions such as:

$$CO_2 + \text{coke} \rightarrow 2CO \quad \text{(Reaction 4)}$$

but negatively impacts equilibrium by allowing competing net reactions, such as;

$$CO_2 + CH_4 \leftrightarrow CO + 2H_2 \quad \text{(Reaction 5)}.$$

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step is conducted by contacting the methane-containing feedstock with the dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the reaction zone comprises a plurality of series-connected fluidized bed reactors in which particulate catalyst is cascaded in one direction from one reactor to the next adjacent reactor in the series, while the feed is passed through and between the reactors in the opposite direction.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence in some configurations it may be possible to reduce the difference between the maximum and minimum temperatures to essentially zero. Alternatively, by supplying heated catalyst to the dehydrocyclization reaction, it may be possible to produce an inverse temperature gradient; that is with the process gas outlet reaction temperature being greater than the process gas inlet reaction temperature.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 hr$^{-1}$, such as about 0.1 to about 500 hr$^{-1}$, for example about 1 to about 20 hr$^{-1}$. Conveniently, the dehydrocyclization step is conducted in the absence of $O_2$.

Since the dehydrocyclization reaction is endothermic the present process includes the step of supplying heat to the reaction. This is achieved by withdrawing a first portion of the catalyst from the reaction zone, either on an intermittent or a continuous basis, and transferring it to a separate heating zone, where the first catalyst portion is heated by direct contact with hot combustion gases generated by burning a supplemental source of fuel. The heated first catalyst portion is then returned to the reaction zone.

By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, the use of an oxygen-lean atmosphere inhibits oxidation of metal carbides present in the dehydrocyclization catalyst and minimizes the average steam partial pressure thereby reducing catalyst hydrothermal aging.

Alternatively, a suitable supplemental fuel source is hydrogen and, in particular, part of the hydrogen generated as a by-product of the aromatization reaction.

Conveniently, said first catalyst portion is contacted directly with the burning source of fuel in the heating zone. Alternatively, the source of fuel is burned in a combustion zone separate from said heating zone and the combustion gases generated in the combustion zone are fed to the heating zone to heat the first catalyst portion.

In one practical embodiment, the heating zone is elongated and the first catalyst portion is passed through the heating zone from an inlet at or adjacent one end of the heating zone to an outlet at or adjacent the other end of the heating zone, with heat being applied to first catalyst portion at a plurality of locations spaced along the length of the heating zone. In this way, the heat input to the first catalyst portion can be distributed along the length of the heating zone thereby minimizing catalyst surface temperatures and internal gradients.

Where the first catalyst portion is heated by direct contact with the burning source of fuel in the heating zone, gradual heating of the catalyst can be achieved by supplying substantially all of the supplemental fuel to the inlet end of the heating zone and then supplying the oxygen-containing gas incrementally to said heating zone at said plurality of spaced locations along the length of heating zone. Alternatively, substantially all of the oxygen-containing gas required to burn said supplemental fuel can be supplied to the inlet end of the heating zone and the supplemental fuel supplied incrementally to the heating zone at said plurality of spaced locations.

Where the first catalyst portion is heated by direct contact with hot combustion gases generated in a separate combustion zone, gradual heating of the catalyst can be achieved by supplying the hot combustion gases to said plurality of spaced locations along the length of heating zone.

In one embodiment, the heating zone is a riser and said first catalyst portion is passed upwardly through the riser during the reheating step. In practice, the heating zone may include a plurality of risers connected in parallel. Alternatively, said heating zone can include a moving bed of said catalyst.

Typically, the first catalyst portion is at a temperature of about 500° C. to about 900° C. on entering the heating zone and is at a temperature of about 800° C. to about 1000° C. on leaving the heating zone. The hot combustion gases are typically at a temperature of less than 1300° C., generally less than 1100° C., for example less than 1000° C., and conveniently at a temperature in the range of about 800° C. to less than 1000° C. Typically, the heating zone will be operated at pressures between 10 and 100 psia (69 and 690 kPa), such as between 15 and 60 psia (103 and 414 kPa). Typically, the average residence time of catalyst particles in the heating zone will be between 0.1 and 100 seconds, such as between 1 and 10 seconds.

Prior to being reintroduced into the reaction zone and, generally after passage through the heating zone, the first catalyst portion may be subjected to one or more stripping steps to at least partially remove (a) coke or heavy hydrocarbons that may have been produced on the surface of the catalyst and/or (b) water or oxygen that may have been adsorbed by the catalyst. Stripping to remove coke or heavy hydrocarbons, which is generally referred to as regeneration, is conveniently effected by contacting the first catalyst portion with steam, hydrogen and/or $CO_2$ in a regeneration zone whereas stripping to remove water or oxygen is conveniently effected by contacting the first catalyst portion with methane, $CO_2$ or hydrogen.

In addition, since the reheating step may tend to oxidize catalytically active metal species, particularly metal carbides, contained by the first catalyst portion, the reheated catalyst may be subjected to a carburizing step prior to being reintroduced into the reaction zone. Conveniently, the carburization step is effected by contacting the first catalyst portion with $H_2$, and CO, $CO_2$, and/or a hydrocarbon, such as methane, ethane, or propane, and can be conducted simultaneously with or separately from the water/oxygen stripping step. Conveniently, carburization of the reheated catalyst is effected in the catalyst treatment zone discussed in detail below.

As well as being endothermic, the dehydrocyclization reaction tends to deposit coke on the catalyst and hence, to maintain the activity of the dehydrocyclization catalyst, a second portion of the catalyst may be withdrawn from the reaction zone, either on an intermittent or a continuous basis, and transferred to a separate regeneration zone. The gas used to transport the second catalyst portion to the regeneration zone may contain $O_2$ but preferably contains less $O_2$ than air, such as less than 10 wt % $O_2$, for example less than 5% $O_2$. The transporting gas may contain $CO_2$ and/or $H_2$ to gasify a portion of the coke from the second catalyst portion, but typically is substantially free of $H_2O$ and is at a low temperature (typically less than 200° C.) so that the catalyst stream does not oxidize and heat up above the target maximum temperature of the regeneration zone.

In the regeneration zone, the second catalyst portion is typically contacted with an oxygen-containing gas under conditions to at least partially remove the coke on the catalyst and thereby regenerate the catalyst. The regeneration gas normally contains less $O_2$ than air, such as less than 10 wt %, for example less than 5 wt %, $O_2$, and is typically substantially free of $H_2O$. The regeneration gas may also contain $CO_2$ to gasify a portion of the coke from the second catalyst portion. Convenient sources of the regeneration gas are an $O_2$ depleted, $N_2$ enriched stream from an air separation unit and a high $CO_2$ reject stream from industrial or natural gas processing to which air or $O_2$ has been added to achieve the target $O_2$ concentration. Typically the regeneration gas is circulated between the regeneration zone and a conditioning zone, where the used regeneration gas is cooled to condense out excess water, make-up oxygen-containing gas (preferably air) is added to maintain the target $O_2$ concentration and a portion is purged to maintain constant pressure. Typically the regeneration zone will be operated at pressures between 10 and 100 psia (69 and 690 kPa), such as between 15 and 60 psia (103 and 414 kPa).

Alternately the regeneration or catalyst coke stripping may be done utilizing a hydrogen-containing gas. The regeneration conditions when utilizing hydrogen comprise a temperature from about 600° C. to about 1000° C., such as from about 700° C. to about 950° C., for example from about 800° C. to about 900° C. Generally, the hydrogen-containing gas does not contain significant quantities of methane or other hydrocarbons; typically with the hydrocarbon content being less than 20 mol %, such as less than 10 mol %, for example less than 2 mol %.

The regeneration zone may be a reactor operated as a fluidized bed, an ebulating bed, a settling bed, a riser reactor or a combination thereof. In practice, the regeneration zone may include a plurality of reactors, such as a plurality of riser reactors connected in parallel or a plurality of reactors connected in series such as a riser reactor followed by a settling bed. The catalyst regeneration reactions are exothermic and hence the regeneration zone should be operated at the lowest temperature required to remove the required amount of coke at the design residence time and in particular so that the temperature does not exceed the point at which metal oxide volatilization occurs or the catalyst substrate undergoes rapid deterioration. Generally, the conditions in the regeneration zone are controlled so that the maximum temperature reached in the regeneration zone is less than the maximum temperature of the dehydrocyclization reaction zone and typically the maximum regeneration zone temperature is from about 400° C. to about 900° C., such as from about 500° C. to about 700° C. The minimum temperature in the regeneration zone is typically from about 300° C. to about 500° C.

Catalyst residence time in the regeneration zone also should be minimized to reduce catalyst aging rate and maximize percent of time the catalyst spends in the reactor doing useful work. Typically, the average residence time of catalyst particles in the regeneration zone will be between 0.1 and 100 minutes, for example between 1 and 20 minutes.

Conveniently, the ratio of the weight of the first catalyst portion transferred in a given time to the heating zone to the weight of second catalyst portion transferred in the same time to the regeneration zone is in the range of about 5:1 to about 100:1, such as about 10:1 to about 20:1.

In addition to removing coke on the catalyst, the oxygen-containing gas in the regeneration zone tends to react with the metal on the catalyst, thereby converting the metal from the elemental or carbidic species desired for the dehydroaromatization reaction to less active oxide species. Moreover, and particularly where the support is a zeolite, the regeneration step may produce active sites on the surface of the catalyst support that favor coke deposition. Thus, before being returned to the reaction zone, the regenerated catalyst is transferred to a catalyst treatment zone separate from the regeneration zone, the heating zone and the reaction zone, where the regenerated catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, CO, $H_2$, $H_2O$ and inert diluents. Alternatively, the carburizing gas may be a mixture of hydrogen and at least one of CO and $CO_2$. Moreover, it may be desirable to contact the regenerated catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the regenerated catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can supplied to the regenerated catalyst and/or the carburizing gas prior to or during the carburization step. For example heat can be supplied to the regenerated catalyst by indirect heating, by contacting with hot flue gas from the reaction zone or the heating zone, by contacting with the hot gaseous effluent from the carburization process, or by mixing with the heated first catalyst portion from the heating zone. The latter heating method may be preferred since this can also allow recarburization of the first catalyst portion which may have been oxidized in the heating zone. Heat is conveniently supplied to the carburization gas by means of an external furnace or heat exchanger or by direct contact with the heated first catalyst portion prior to mixing with the regenerated catalyst.

The catalyst treatment zone may be operated as a fluidized bed reactor, ebulating bed reactor, settling bed reactor, riser reactor or circulating riser reactor. In one embodiment, the catalyst treatment zone comprises a settling bed reactor. Alternatively, the catalyst treatment zone comprises a single fluidized bed reactor with internal baffles to prevent backmixing or a plurality of fluidized bed reactors in series with the regenerated catalyst being cascaded between adjacent reactors. In any event, contact in the catalyst treatment zone is facilitated by arranging that the regenerated catalyst and the carburizing gas flow in opposite directions in said catalyst treatment zone. Employing such a countercurrent flow, a temperature profile may be developed in the catalyst treatment zone such that carburization of the regenerated catalyst initially occurs at a low temperature but the carburization temperature increases as the catalyst flows through the bed.

For some catalysts, it may be desirable that the regenerated catalyst portion is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

In one practical embodiment, the dehydrocyclization step is conducted in a vertically-disposed, settling bed reactor with the feedstock entering the reactor at or near its base and the heated first catalyst portion and the regenerated second catalyst portion being returned to the reactor at or near the top of the reactor. Conveniently, said first and second catalyst portions are removed from at or near the base of the reactor and the process effluent is recovered from at or near the top of the reactor.

In an alternative embodiment, the dehydrocyclization step is conducted in a plurality of fluidized bed reactors connected in series, with the feedstock entering the first reactor in the series and the heated first catalyst portion and the regenerated second catalyst portion being returned to the final reactor in the series. Conveniently, said first and second catalyst portions are removed from the first reactor.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, such as at least 30 wt %, more aromatic rings than the feed.

The benzene and naphthalene are then recovered from the dehydrocyclization effluent, for example, by solvent extraction followed by fractionation. However, as will be discussed below, at least part of these aromatic components can be submitted to an alkylation step, before or after product recovery, to produce higher value materials, such as xylenes.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Serial No. PCT/US2005/044042 (Attorney Docket No. 2004B154), filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 6)}$$

$$2CO_2 + 7H_2 \leftrightarrow C_2H_6 + 4H_2O \quad \text{(Reaction 7)}$$

The carbon dioxide employed is conveniently part of a natural gas stream and typically the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2$:$CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5+$, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \quad \text{(Reaction 8)}$$

and by the following reaction:

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, for example from about 500 $hr^{-1}$ to about 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:

i) at least one metal from Group 3 and at least one metal from Groups 4-15 of the Periodic Table of the Elements;

ii) at least one metal from Groups 5-15 of the Periodic Table of the Elements, and at least one metal from at least one of Groups 1, 2, and 4 of the Periodic Table of the Elements;

iii) at least one metal from Groups 1-2, at least one metal from Group 3, and at least one metal from Groups 4-15 of the Periodic Table of the Elements; and iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

The major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, (Attorney Docket No. 2004B156), filed on Dec. 2, 2005 and PCT/US2005/044038, (Attorney Docket No. 2004B155), filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more for example about 500 $hr^{-1}$ to about 10,000 $hr^{-1}$.

The effluent from the reverse shift reactor can then be fed to an alkylation reactor operating under conditions to cause reactions such as the following to occur:

$$CO+2H_2 \leftrightarrow CH_3OH \qquad \text{(Reaction 9)}$$

$$CH_3OH+C_6H_6 \rightarrow toluene+H_2O \qquad \text{(Reaction 10)}$$

$$2CH_3OH+C_6H_6 \rightarrow xylenes+2H_2O \qquad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr 1, such as about 2 to about 10 $hr^{-1}$.

The invention will now be more particularly described with reference to the accompanying drawings and the following non-limiting Examples.

Referring to FIG. 1, the drawing illustrates a simplified design of a dehydrocyclization reactor, with a catalyst reheater and a catalyst regenerator, for converting methane to aromatics according to a first embodiment of the invention. In this embodiment, the dehydrocyclization reactor includes a vertically disposed settling bed reactor 11, into which heated catalyst flows through an inlet 12 located adjacent the top of the reactor 11 and from which cooled catalyst flows by way of first and second outlets 13, 14 respectively located adjacent the base of the reactor 11. Methane feed 15 is introduced into the reactor 11 adjacent the base thereof. Typically, the heated catalyst enters the reactor 11 at a temperature of about 900° C. and the cooled catalyst leaves the reactor at a temperature of about 650° C.

A first portion of the cooled catalyst flows under gravity from the first outlet 13 to the base of a riser reheater 16, where the catalyst is entrained in a mixture of air and methane fuel passed into the riser through a manifold 17. The catalyst is transported up the riser 16 by the air/methane mixture and is heated during its passage through the riser 16 by combustion of the methane. The mixture entering the riser 16 through the manifold 17 contains all the fuel required to heat the catalyst to the required reaction temperature, but is deficient in oxygen. Additional air is therefore introduced into the riser 16 through a plurality of inlets 18 spaced along the length of the riser (for simplicity only two inlets 18 are indicated in FIG. 1 but in reality the number may be far greater), whereby heating of the catalyst occurs gradually as the catalyst flows up through the riser 16.

On exiting the top of the riser 16, the heated catalyst passes into a separator 19 where the solid particulate catalyst is separated from the combustion gases and then passed to a catalyst treatment unit 21. The combustion gases are then fed to cyclones 22 for removal of catalyst fines before being subjected to heat recovery. Using air as the combustion medium in the reheater 16, the combustion gases typically comprise 67.9 wt % $N_2$, 0.2 wt % $O_2$, 1.3 wt % $H_2$, 3.6 wt % CO, 7.9 wt % $CO_2$, and 17.3 wt % $H_2O$.

A second portion of the cooled catalyst flows under gravity from the second outlet 14 to the base of a riser regenerator 23 where the catalyst is entrained in a stream of oxygen-containing gas and transported up the riser regenerator. As the second catalyst portion passes through the regenerator 23 coke generated on the catalyst in the dehydrocyclization reactor 11 is burned off the catalyst thereby heating the catalyst. However, the regenerator 23 is conveniently controlled, for example by passing the oxygen-containing gas fed to the regenerator 23 through cooling coils or other cooling means, so that the temperature of the second catalyst portion exiting the regenerator 23 is less than the temperature of the second catalyst portion exiting the reactor 11. Typically, the temperature of the second catalyst portion exiting the regenerator 23 is about 550° C. whereas on exiting the reactor 11 the second catalyst portion is at a temperature of about 650° C.

On exiting the top of the regenerator 23, the second catalyst portion passes into a separator 24 where the solid particulate catalyst separates from the combustion gasses, which are then fed to the cyclones 22 for removal of catalyst fines. The separated catalyst particles then flow to the catalyst treatment unit 21.

In the catalyst treatment unit 21, the regenerated catalyst is initially contacted with one or more hydrocarbon streams 25, such as methane, ethane or propane as well as $H_2$ and/or CO flowing upwardly from lower parts of the vessel, to recarburize the metal on the catalyst. The catalyst is then contacted with a methane stream 26 to remove water or oxygen that may have been adsorbed by the catalyst. The regenerated catalyst is then combined with the reheated catalyst from the riser 16 and the combined catalyst is contacted with a hydrogen and/or $CO_2$ stream 27 remove any residual coke or heavy hydrocarbons. After stripping the catalyst, the hot gasses flow upward to help heat the regenerated catalyst portion in the recarburization section. The combined catalyst is then returned to the reactor 11 through the inlet 12. The flue gases generated in the catalyst treatment unit 21 can be used as to supplement the methane fuel supplied to the riser reheater 16 or can be used in other parts of the process.

The following non-limiting examples are presented to illustrate the advantages of performing carburization of the dehydrocyclization catalyst in a separate vessel from the dehydrocyclization reactor so that carburization conditions (temperature, composition, flow rate, and time) can be optimized. Actual carburization conditions used in practice will be dependent on the composition of the dehydrocyclization catalyst (metal and substrate).

EXAMPLE 1

This example demonstrates the use of pre-carburization of $MoO_3$-loaded ZSM-5 catalysts in order to achieve optimal performance for the methane dehydrocyclization reaction to benzene. Specifically, pre-carburization can result in increased methane conversion, higher benzene yield and selectivity, and lower coke make. Pre-carburization of $MoO_3$-loaded ZSM-5 using carbon and hydrogen containing feeds at optimal temperature results in reduction and carburization of $MoO_3$ to "active" $MoO_xC_y$ species. The state and dispersion of this active metal species depends on the pre-carburization conditions.

Mo/ZSM-5 catalysts were prepared via impregnation of required amount of ammonium heptamolybdate solution onto $NH_4$ZSM-5 support (having a $Si/Al_2$ ratio of 28) via incipient wetness, followed by drying at 120° C. for 2 hours and final calcination at 500° C. for 6 hours in flowing air. The molybdenum loading (wt % metal basis) was varied by varying the ammonium heptamolybdate concentration of the impregnating solution. Several molybdenum loadings were prepared from 1.5 to 7.0 wt % Mo.

Catalytic testing of the Mo/ZSM-5 catalysts was performed using a Tapered-Element Oscillating Microbalance (TEOM), allowing accurate determination of catalyst mass changes during reaction with fast response times. Each Mo/ZSM-5 catalyst sample (after calcination) was pelletized, crushed and sieved to 30-60 mesh particle size. Approximately 0.10 grams of sieved catalyst particles were loaded into the TEOM sample holder (0.20 cc total sample volume), and packed to form a fixed-bed using quartz wool supports. Certain of the samples were purged and dried at 150° C. for 30 min using helium and then heated to reaction temperature, without pre-carburization.

Other samples were pre-carburized using about 11 cc[STP]/min of a 10% n-hexane/helium feed (prepared by bubbling helium through a hexane saturator at 10° C.) as the carburizing gas. The catalyst was first heated from 150° C. to 500° C. under helium. After stabilization at 500° C. for 10 min, the 10% n-hexane/helium feed was passed over the catalyst for about 35 min (until about 1 wt % mass change was observed on the TEOM). The reactor was then purged with helium for 5 min, followed by heating to reaction temperature of 800° C. for methane dehydrocyclization testing.

Catalyst performance for methane dehydrocyclization to benzene was performed at 800° C. using a 95% $CH_4$-5% Ar feed (Ar is used as internal standard) at a weight-hourly space velocity (based on methane) of 4 $hr^{-1}$. The reaction effluent was analyzed using a mass spectrometer to determine the methane, benzene, naphthalene, hydrogen and argon concentrations. The rate of coke deposition on the catalyst (i.e., heavy carbonaceous deposit which does not volatize from catalyst surface) was determined directly via mass changes observed using the microbalance. Table 1 compares the performance of the Mo/ZSM-5 catalysts (with varying Mo loadings) with or without pre-carburization.

TABLE 1

| Run | Wt % Mo | Treatment | Benzene Productivity (g bz/g catalyst) | CH$_4$ Conversion (g CH$_4$/g catalyst) | Benzene Selectivity (wt %) |
|---|---|---|---|---|---|
| A | 1.5 | No Precarburization | 0.12 | 0.37 | 32 |
| B | 1.5 | Precarburization | 0.15 | 0.45 | 33 |
| C | 2.7 | No Precarburization | 0.16 | 0.40 | 40 |
| D | 2.7 | Precarburization | 0.21 | 0.46 | 46 |
| E | 5 | No Precarburization | 0.20 | 0.42 | 48 |
| F | 5 | Precarburization | 0.31 | 0.64 | 48 |
| G | 7 | No Precarburization | 0.02 | 0.12 | 15 |
| H | 7 | Precarburization | 0.44 | 0.61 | 54 |

The values reported in Table 1 for catalyst performance (e.g., benzene productivity, methane converted, benzene selectivity) are cumulative or average values for the time period beginning at methane injection and ending when the instantaneous benzene selectivity declines to 20%.

As can be observed from Table 1, pre-carburization of Mo/ZSM-5 catalysts results in higher cumulative benzene productivity (total grams of benzene produced per gram of catalyst) for each of the Mo loading levels. The % increase in benzene productivity with pre-carburization is more pronounced at higher Mo loadings—increase by 20% for 1.5% Mo level compared to 55% increase for 5% Mo level. There is also a significant increase in the total amount of methane converted and relatively smaller increase in benzene selectivity indicating a greater number of active sites for the pre-carburized samples. Runs A, C, E and G (for various Mo loadings with no pre-carburization) indicate that as the Mo loading is increased, benzene productivity increases until ~5% Mo loading, followed by a sharp decline at 7%. However, the analogous runs for pre-carburized samples (Runs B, D, F, and H) show a continuous increase in benzene productivity with Mo loading. This suggests that pre-carburization of MoO$_3$ at lower temperature (500 versus 800° C.) minimizes detrimental interactions between MoO$_3$ and the zeolite that may occur on heating to higher temperatures (especially at higher Mo loadings). This results in greater number of active sites and significantly improved performance.

EXAMPLE 2

Table 2 shows the effect of various carburizing pretreatments on the resulting performance for 7% Mo/ZSM-5 (as synthesized in Example 1). Run G (in Table 2) shows the base case performance with no pre-carburization/pretreatment prior to testing at 800° C. Run H shows the results for pre-carburization at 500° C. using 10% hexane in helium (as described in Example 1).

Low-temperature, hydrogen reduction at 500° C. (in Run I) was performed using 10 cc/min of pure hydrogen for about 45 min. Hydrogen reduction of MoO$_3$ species to oxygen-deficient MoO$_x$ species increases benzene productivity from 0.02 to 0.18 g/g, increases methane conversion from 0.12 to 0.51 g/g, and increases benzene selectivity from 15 to 35 wt %.

Carburizing the MoO$_3$ species using 10% hexane in helium feed at different temperatures (725° C. for Run J, 650° C. for Run L and 500° C. for Run H) indicates that lowering carburization temperature improves catalyst performance. The benzene productivity, selectivity and methane conversion increase with decreasing carburization temperature. Moreover, the coke selectivity was also found to decrease with pre-carburization temperature. Lowering the pre-carburization temperature minimizes detrimental interaction between MoO$_3$ and zeolite at higher temperatures (e.g., dealumination of zeolite to form aluminum molybdate) and decreases the amount of excess coke deposited on the catalyst (since less carbon species are desorbed during heat-up to 800° C. under helium flow).

Run K and M utilize methane to carburize the MoO$_3$ species. Heating in 95% CH$_4$—Ar from 650 to 800° C. with ramp rate of 5 C/min (Run K) shows inferior performance compared to carburization performed using 15% CH$_4$—H$_2$ from 300 to 650° C. with ramp rate of 5 C/min (Run M). The use of methane and hydrogen gas mixture allows carburization of Mo to proceed without formation of excess graphitic coke (since the required carbon activity for converting Mo to Mo$_2$C is lower than that required for coke formation (equal to unity)). The lower carburization temperatures and reduced coke deposition may explain the superior performance of Run M compared to Run K. Run M and H give the optimal performance for 7% Mo/ZSM-5 with significantly improved benzene productivity and very low coking rates.

TABLE 2

| Run | Catalyst Treatment | Benzene Productivity (g bz/g catalyst) | CH$_4$ Conversion (g CH$_4$/g catalyst) | Benzene Selectivity (wt %) | Coke Selectivity (wt %) |
|---|---|---|---|---|---|
| G | No Precarburization | 0.02 | 0.12 | 15 | n/a |
| H | Carburize with 10% hexane/He (500° C.) | 0.44 | 0.81 | 54 | 11 |
| I | Reduce with H$_2$ (500° C.) | 0.18 | 0.51 | 35 | 22 |
| J | Carburize with 10% hexane/He (725° C.) | 0.14 | 0.33 | 42 | 18 |
| K | Carburize with CH$_4$ (Ramp from 650° C. to 800° C.) | 0.25 | 0.54 | 46 | 12 |
| L | Carburize with 10% hexane/He (660° C.) | 0.34 | 0.67 | 51 | 13 |
| M | Carburize with 15% CH$_4$/H$_2$ (Ramp from 300° C. to 650° C.) | 0.43 | 0.81 | 53 | 13 |

EXAMPLE 3

Table 3 shows the effect of various pretreatments on the resulting performance for 2.7% Mo/ZSM-5 (as synthesized in Example 1). Run C (in Table 3) shows the base case performance with no pre-carburization/pretreatment prior to testing at 800° C. Run D shows the results for pre-carburization at 500° C. using 10% hexane in helium (as described in Example 1). Run N attempted to eliminate the initial induction period via a brief pre-carburization of 2.7% Mo/ZSM-5 at 800° C. using 95% CH$_4$—Ar feed. As expected the benzene productivity did not increase, however the benzene selectivity increased from 40 to 44 wt % and the coke selectivity decreased from 26 to 20 wt %. This approach has the benefit of allowing non-selective, pre-carburization reactions (which generate hydrogen and other by-products) to occur in a separate reactor vessel thereby not adversely impacting benzene thermodynamic yield. Lowering the carburization temperature using 15% $CH_4$—$H_2$ carburization from 300 to 650° C. (Run O) or 10% $C_2H_6$—$CH_4$ carburization at 600° C. (for time required for 1 wt % mass change) (Run P) or 10% hexane in helium feed at 500° C. (Run D) increases benzene productivity from 0.16 to about 0.21 g/g and benzene selectivity from 40 to about 46%.

TABLE 3

| Run | Catalyst Treatment | Benzene Productivity (g bz/g catalyst) | $CH_4$ Conversion (g $CH_4$/g catalyst) | Benzene Selectivity (wt %) | Coke Selectivity (wt %) |
|---|---|---|---|---|---|
| C | No Precarburization | 0.16 | 0.40 | 40 | 26* |
| D | Carburize with 10% hexane/He (500° C.) | 0.21 | 0.46 | 46 | 23 |
| N | Carburize with $CH_4$ (800° C.) | 0.15 | 0.34 | 44 | 20 |
| O | Carburize with 15% $CH_4/H_2$ (Ramp from 300° C. to 650° C.) | 0.19 | 0.45 | 42 | 25 |
| P | Carburize with 10% $C_2H_6/CH_4$ (600° C.) | 0.22 | 0.47 | 47 | 23 |

*Accounting for additional weight loss due to $MoO_3$ reduction

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting methane to higher hydrocarbons including aromatic hydrocarbons, the process comprising:
  (a) contacting a feed containing methane with a dehydrocyclization catalyst in a reaction zone under conditions comprising a first maximum temperature and effective to convert said methane to aromatic hydrocarbons and generate coke on the catalyst;
  (b) transferring a portion of said catalyst from the reaction zone to a regeneration zone separate from said reaction zone;
  (c) contacting said catalyst portion with a regeneration gas in said regeneration zone under conditions effective to at least partially remove coke from said catalyst portion and comprising a second maximum temperature less than or equal to said first maximum temperature;
  (d) contacting the regenerated catalyst portion with a carburizing gas in a catalyst treatment zone separate from said reaction zone under conditions comprising a third maximum temperature less than or equal to said first maximum temperature, wherein said carburizing gas comprises at least one hydrocarbon; and
  (e) returning the catalyst portion to the reaction zone.

2. The process of claim 1, wherein said third maximum temperature is greater than said second maximum temperature.

3. The process of claim 1, wherein said first maximum temperature is from about 700° C. to about 1200° C.

4. The process of claim 1, wherein said first maximum temperature is from about 800° C. to about 950° C.

5. The process of claim 1, wherein said second maximum temperature is from about 400° C. to about 900° C.

6. The process of claim 1, wherein said second maximum temperature is from about 500° C. to about 700° C.

7. The process of claim 1, wherein said third maximum temperature is from about 400° C. to about 1100° C.

8. The process of claim 1, wherein said third maximum temperature is from about 500° C. to about 900° C.

9. The process of claim 1, wherein heat is supplied to said regenerated catalyst portion and/or said carburizing gas prior to or during said contacting (d).

10. The process of claim 1, wherein said catalyst portion and said carburizing gas flow in opposite directions in said catalyst treatment zone.

11. The process of claim 1, wherein said catalyst treatment zone is operated as a settling bed reactor.

12. The process of claim 1, wherein said catalyst treatment zone comprises one or more fluidized bed reactors.

13. The process of claim 1, wherein said carburizing gas comprises at least one of methane, ethane, propane, butane, isobutene, hexane, benzene and naphthalene.

14. The process of claim 13, wherein said carburizing gas also comprises at least one of $CO_2$, CO, $H_2$, H2O and inert diluents.

15. The process of claim 1, wherein said carburizing gas also comprises hydrogen and at least one of CO and $CO_2$.

16. The process of claim 1, wherein said contacting (d) comprises reacting said regenerated catalyst portion sequentially with a plurality of carburizing gases supplied to the carburization zone at one or more locations.

17. The process of claim 16, wherein each of said plurality of carburizing gases comprises at least one hydrocarbon and a mixture of hydrogen and at least one of CO and $CO_2$.

18. The process of claim 17, wherein said at least one hydrocarbon is selected from methane, ethane, propane, butane, isobutene, hexane, benzene and naphthalene.

19. The process of claim 1, wherein the dehydrocyclization catalyst comprises a metal at least partly present in elemental form or as a carbide species during the contacting (a), wherein the contacting (c) at least partly converts said metal to an oxide form, and the contacting (d) at least partly returns the metal to the elemental or carbide form.

20. The process of claim 19, wherein the metal comprises at least one of molybdenum, tungsten, zinc and rhenium.

21. The process of claim 1, wherein said dehydrocyclization catalyst also comprises an inorganic support.

22. The process of claim 21, wherein said inorganic support comprises ZSM-5, silica or an aluminum oxide.

23. A process for converting methane to higher hydrocarbons including aromatic hydrocarbons, the process comprising:
  (a) contacting a dehydrocyclization catalyst with a carburizing gas under carburizing conditions in a catalyst treatment zone, wherein said carburizing gas comprises at least one hydrocarbon;
  (b) transferring said dehydrocyclization catalyst portion from (a) to a reaction zone separate from the catalyst treatment zone; and (c) contacting a feed containing methane with said dehydrocyclization catalyst in the reaction zone under dehydrocyclization conditions effective to convert said methane to aromatic hydrocarbons,
wherein said dehydrocyclization conditions comprise a first maximum temperature and said carburizing conditions comprise a further maximum temperature less than or equal to the first maximum temperature.

24. The process of claim 23, wherein said first maximum temperature is from about 700° C. to about 1200° C.

25. The process of claim 24, wherein said further maximum temperature is from about 400° C. to about 1100° C.

26. The process of claim 23, wherein said first maximum temperature is from about 800° C. to about 950° C.

27. The process of claim 26, wherein said further maximum temperature is from about 500° C. to about 900° C.

28. The process of claim 23, wherein said carburizing gas comprises at least one of methane, ethane, propane, butane, isobutene, hexane, benzene and naphthalene.

29. A process for converting methane to higher hydrocarbons including aromatic hydrocarbons, the process comprising:
(a) contacting a feed containing methane with a dehydrocyclization catalyst in a reaction zone under conditions effective to convert said methane to aromatic hydrocarbons and generate coke on the catalyst, said conditions comprising a first maximum temperature and said dehydrocyclization catalyst including a metal at least partly present in elemental form or as a carbide species;
(b) transferring a first portion of said catalyst from the reaction zone to a heating zone separate from said reaction zone;
(c) heating the first catalyst portion in the heating zone by direct contact of the catalyst with hot combustion gases generated by burning a supplemental source of fuel;
(d) transferring a second portion of said catalyst from said reaction zone to a regeneration zone separate from said reaction zone and said heating zone;
(e) contacting said second catalyst portion with a regeneration gas in said regeneration zone under conditions comprising a second maximum temperature less than or equal to said first maximum temperature and effective to at least partially remove coke from said second catalyst portion and to at least partly convert the metal of said second catalyst portion to an oxide species;
(f) transferring the regenerated second catalyst portion from the regeneration zone to a catalyst treatment zone separate from the reaction zone, the heating zone and the regeneration zone;
(g) contacting the regenerated second catalyst portion with a carburizing gas in said catalyst treatment zone under conditions effective to at least partly return the metal of said second catalyst portion to an elemental form or to a carbide species, wherein said carburizing gas comprises at least one hydrocarbon; and
(h) returning the first and second catalyst portions to the reaction zone.

30. The process of claim 29, wherein the ratio of the weight of the first catalyst portion transferred in a given time to said heating zone to the weight of second catalyst portion transferred in the same time to the regeneration zone is in the range of about 5:1 to about 100:1.

31. The process of claim 29, wherein the heated first catalyst portion is also transferred to the catalyst treatment zone for contacting with a carburizing gas.

32. The process of claim 31, wherein said carburizing gas comprises at least one of methane, ethane, propane, butane, isobutene, hexane, benzene and naphthalene.

33. The process of claim 31, wherein said carburizing gas also comprises at least one of $CO_2$, CO, $H_2$, $H_2O$ and inert diluents.

34. The process of claim 29, wherein said carburizing gas also comprises hydrogen and at least one of CO and $CO_2$.

35. The process of claim 29, wherein said first maximum temperature is about 700° C. to about 1200° C.

36. The process of claim 29, wherein said second maximum temperature is from about 400° C. to about 900° C.

37. The process of claim 29, wherein said conditions in (g) comprise a third maximum temperature less than said first maximum temperature.

38. The process of claim 37, wherein said third maximum temperature is greater than said second maximum temperature.

39. The process of claim 37, wherein said third maximum temperature is from about 400° C. to about 1100° C.

40. A process for converting methane to higher hydrocarbons including aromatic hydrocarbons, the process comprising:
(a) contacting a feed containing methane with a dehydrocyclization catalyst in a reaction zone with an inverse temperature profile under conditions effective to convert said methane to aromatic hydrocarbons and generate coke on the catalyst, and said dehydrocyclization catalyst including a metal at least partly present in elemental form or as a carbide species;
(b) transferring a portion of said catalyst from the reaction zone to a heating zone separate from said reaction zone;
(c) heating the catalyst portion in the heating zone by direct contact of the catalyst with hot combustion gases generated by burning a supplemental source of fuel;
(d) contacting said heated catalyst portion with a regeneration gas in a regeneration zone under conditions effective to at least partially remove coke from said catalyst portion;
(e) transferring the regenerated catalyst portion from the regeneration zone to a catalyst treatment zone separate from the reaction zone, the heating zone and the regeneration zone;
(f) contacting the regenerated catalyst portion with a carburizing gas in said catalyst treatment zone under conditions effective to at least partly return the metal of said catalyst portion to an elemental form or to a carbide species, wherein said carburizing gas comprises at least one hydrocarbon; and
(g) returning the catalyst portion to the reaction zone.

41. The process of claim 40 and further comprising introducing fresh dehydrocyclization catalyst to the process at (f).

42. The process of claim 40, wherein said carburizing gas comprises at least one of methane, ethane, propane, butane, isobutene, hexane, benzene and naphthalene.

43. The process of claim 40, wherein said carburizing gas also comprises at least one of $CO_2$, CO, $H_2$, $H_2O$ and inert diluents.

44. The process of claim 40, wherein said carburizing gas also comprises hydrogen and at least one of CO and $CO_2$.

45. A process for converting methane to higher hydrocarbons including aromatic hydrocarbons, the process comprising:
(a) introducing a fresh metal-containing dehydrocyclization catalyst portion to a catalyst treatment zone;
(b) contacting the fresh dehydrocyclization catalyst with a carburizing gas in said catalyst treatment zone under conditions effective to at least partly convert the metal of said catalyst to an elemental form or to a carbide species and/or reduce coke-selective sites, wherein said carburizing gas comprises at least one hydrocarbon;

(c) transferring said treated dehydrocyclization catalyst from the catalyst treatment zone to a reaction zone separate from the catalyst treatment zone;

(d) contacting a feed containing methane with said treated dehydrocyclization catalyst in said reaction zone under conditions effective to convert said methane to aromatic hydrocarbons and generate an inverse temperature profile in the reaction zone;

(e) transferring a portion of said catalyst from the reaction zone to a heating zone separate from said reaction zone and the catalyst treatment zone;

(f) heating the catalyst portion in the heating zone by direct contact of the catalyst portion with hot combustion gases generated by burning a supplemental source of fuel; and (g) returning the catalyst portion to the reaction zone.

46. The process of claim 45, wherein said carburizing gas comprises at least one of methane, ethane, propane, butane, isobutene, hexane, benzene and naphthalene.

47. The process of claim 45, wherein said carburizing gas also comprises at least one of $CO_2$, CO, $H_2$, $H_2O$ and inert diluents.

48. The process of claim 45, wherein said carburizing gas also comprises hydrogen and at least one of CO and $CO_2$.

49. A process for converting methane to higher hydrocarbons including aromatic hydrocarbons, the process comprising:

(a) contacting a feed containing methane with a dehydrocyclization catalyst in a reaction zone with an inverse temperature profile under conditions comprising a maximum temperature and effective to convert said methane to aromatic hydrocarbons;

(b) transferring a portion of said catalyst from the reaction zone to a heating zone separate from said reaction zone;

(c) heating the catalyst portion in the heating zone by direct contact of the catalyst portion with hot combustion gases generated by burning a supplemental source of fuel;

(d) returning the heated catalyst portion to the reaction zone; and (e) introducing fresh dehydrocyclization catalyst to a region of the process at a lower temperature than the maximum temperature of the reaction zone, further characterized by introducing the fresh dehydrocyclization catalyst portion to a catalyst treatment zone separate from said reaction zone and said heating zone and contacting the fresh dehydrocyclization catalyst with a carburizing gas in said catalyst treatment zone, and wherein said carburizing gas comprises at least one hydrocarbon.

50. The process of claim 49, wherein said carburizing gas comprises at least one of methane, ethane, propane, butane, isobutene, hexane, benzene and naphthalene.

51. The process of claim 49, wherein said carburizing gas also comprises at least one of $CO_2$, CO, $H_2$, $H_2O$ and inert diluents.

52. The process of claim 49, wherein said carburizing gas further comprises hydrogen and at least one of CO and $CO_2$.

* * * * *